US008814908B2

(12) United States Patent
Druma et al.

(10) Patent No.: US 8,814,908 B2
(45) Date of Patent: Aug. 26, 2014

(54) INJECTABLE FLEXIBLE INTERSPINOUS PROCESS DEVICE SYSTEM

(75) Inventors: Calin Druma, Cupertino, CA (US); Bruce Chabansky, Palo Alto, CA (US)

(73) Assignee: Warsaw Orthopedic, Inc., Warsaw, IN (US)

(*) Notice: Subject to any disclaimer, the term of this patent is extended or adjusted under 35 U.S.C. 154(b) by 318 days.

(21) Appl. No.: 12/843,322

(22) Filed: Jul. 26, 2010

(65) Prior Publication Data

US 2012/0022590 A1 Jan. 26, 2012

(51) Int. Cl.
*A61B 17/70* (2006.01)

(52) U.S. Cl.
CPC .................................. *A61B 17/7065* (2013.01)
USPC ............................. 606/248; 606/249; 606/279

(58) Field of Classification Search
USPC ............ 606/246–249, 279; 623/17.11–17.16; 600/466–470; 604/508–510
See application file for complete search history.

(56) References Cited

U.S. PATENT DOCUMENTS

| | | |
|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,065,659 A | 11/1962 | Eriksson et al. |
| 3,108,595 A | 10/1963 | Overment |
| 3,426,364 A | 2/1969 | Lumb |
| 3,648,691 A | 3/1972 | Lumb et al. |
| 3,779,239 A | 12/1973 | Fischer et al. |
| 3,867,728 A | 2/1975 | Stubstad et al. |
| 4,011,602 A | 3/1977 | Rybicki et al. |

(Continued)

FOREIGN PATENT DOCUMENTS

| | | |
|---|---|---|
| DE | 2821678 A1 | 11/1979 |
| DE | 3922044 A1 | 2/1991 |

(Continued)

OTHER PUBLICATIONS

"Dispositivo Intervertebrale Ammortizzante DIAM," date unknown, p. 1.

(Continued)

*Primary Examiner* — Pedro Philogene
*Assistant Examiner* — Christina Negrellirodrigue (57) ABSTRACT

An injectable, flexible interspinous process device and a delivery system. The interspinous process device is flexible and can be fillable in situ with a desired amount of biocompatible material. The interspinous process device has a container portion. A support element, such as a self-expanding mesh, is used in conjunction with the container to provide added structural support. The mesh also facilitates deployment of the device when it is properly positioned. A conduit may be coupled to the interspinous process to fill the device. A delivery system is also provided for delivering the flexible interspinous process device to the desired location. The delivery system includes an outer catheter that is disposed over the interspinous process device to maintain it in the undeployed state and thus facilitate delivery of the device to the desired location. An inner removable sleeve and a guidewire may also be used with the delivery system.

20 Claims, 5 Drawing Sheets

(56) References Cited

U.S. PATENT DOCUMENTS

| | | |
|---|---|---|
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,401,112 A | 8/1983 | Rezaian |
| 4,519,100 A | 5/1985 | Wills et al. |
| 4,553,273 A | 11/1985 | Wu |
| 4,554,914 A | 11/1985 | Kapp et al. |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 4,969,888 A | 11/1990 | Scholten et al. |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,171,280 A | 12/1992 | Baumgartner |
| 5,201,734 A | 4/1993 | Cozad et al. |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,360,430 A | 11/1994 | Lin |
| 5,366,455 A | 11/1994 | Dove |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,458,641 A | 10/1995 | Ramirez Jimenez |
| 5,496,318 A | 3/1996 | Howland et al. |
| 5,518,498 A | 5/1996 | Lindenberg et al. |
| 5,549,679 A | 8/1996 | Kuslich |
| 5,554,191 A | 9/1996 | Lahille et al. |
| 5,562,662 A | 10/1996 | Brumfield et al. |
| 5,562,735 A | 10/1996 | Margulies |
| 5,562,736 A | 10/1996 | Ray et al. |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,597 A | 7/1997 | Krapiva |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,454 A | 12/1997 | Baumgartner |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,800,547 A | 9/1998 | Schafer et al. |
| 5,800,549 A | 9/1998 | Bao et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,964,730 A | 10/1999 | Williams et al. |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,066,154 A | 5/2000 | Reiley et al. |
| 6,068,630 A | 5/2000 | Zucherman et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,190,413 B1 | 2/2001 | Sutcliffe |
| 6,190,414 B1 | 2/2001 | Young |
| 6,214,050 B1 | 4/2001 | Huene |
| 6,293,949 B1 | 9/2001 | Justis et al. |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,704 B1 | 7/2002 | Ferree |
| 6,440,169 B1 | 8/2002 | Elberg et al. |
| 6,447,513 B1 | 9/2002 | Griggs |
| 6,451,019 B1 | 9/2002 | Zucherman et al. |
| 6,500,178 B2 | 12/2002 | Zucherman et al. |
| 6,514,256 B2 | 2/2003 | Zucherman et al. |
| 6,520,991 B2 | 2/2003 | Huene |
| 6,554,833 B2 | 4/2003 | Levy et al. |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,685,742 B1 | 2/2004 | Jackson |
| 6,695,842 B2 | 2/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,533 B1 | 5/2004 | Lozier |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,905,512 B2 | 6/2005 | Paes et al. |
| 6,946,000 B2 | 9/2005 | Senegas et al. |
| 6,958,077 B2 | 10/2005 | Suddaby |
| 6,969,404 B2 | 11/2005 | Ferree |
| 6,981,975 B2 | 1/2006 | Michelson |
| 7,011,685 B2 | 3/2006 | Arnin et al. |
| 7,041,136 B2 | 5/2006 | Goble et al. |

(56) References Cited

U.S. PATENT DOCUMENTS

| | | |
|---|---|---|
| 7,048,736 B2 | 5/2006 | Robinson et al. |
| 7,081,120 B2 | 7/2006 | Li et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 2001/0016743 A1 | 8/2001 | Zucherman et al. |
| 2002/0143331 A1 | 10/2002 | Zucherman et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2004/0083002 A1 | 4/2004 | Belef et al. |
| 2004/0087947 A1 | 5/2004 | Lim et al. |
| 2004/0097931 A1 | 5/2004 | Mitchell |
| 2004/0133204 A1 | 7/2004 | Davies |
| 2004/0133280 A1 | 7/2004 | Trieu |
| 2004/0167625 A1 | 8/2004 | Beyar et al. |
| 2004/0199255 A1 | 10/2004 | Mathieu et al. |
| 2004/0260397 A1 | 12/2004 | Lambrecht et al. |
| 2005/0010293 A1 | 1/2005 | Zucherman et al. |
| 2005/0049708 A1 | 3/2005 | Atkinson et al. |
| 2005/0085814 A1 | 4/2005 | Sherman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1* | 4/2006 | Kim ............... 623/17.11 |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0032790 A1 | 2/2007 | Aschmann et al. |
| 2007/0043362 A1 | 2/2007 | Malandain et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0162136 A1 | 7/2007 | O'Neil et al. |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0033251 A1* | 2/2008 | Araghi ............... 600/235 |
| 2008/0058934 A1 | 3/2008 | Malandain et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0183211 A1 | 7/2008 | Lamborne et al. |
| 2008/0183218 A1 | 7/2008 | Mueller et al. |
| 2008/0215094 A1 | 9/2008 | Taylor |
| 2008/0221685 A9 | 9/2008 | Altarac et al. |
| 2008/0262617 A1 | 10/2008 | Froehlich et al. |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0105773 A1 | 4/2009 | Lange et al. |
| 2009/0118833 A1* | 5/2009 | Hudgins et al. ............ 623/17.16 |
| 2009/0216274 A1* | 8/2009 | Morancy-Meister et al. 606/247 |
| 2009/0234389 A1 | 9/2009 | Chuang et al. |
| 2009/0270918 A1 | 10/2009 | Attia et al. |
| 2009/0312806 A1* | 12/2009 | Sherman et al. ............ 606/86 R |
| 2010/0121379 A1 | 5/2010 | Edmond |
| 2010/0262240 A1* | 10/2010 | Chavatte et al. .......... 623/17.11 |

(56) References Cited

U.S. PATENT DOCUMENTS

FOREIGN PATENT DOCUMENTS

| | | |
|---|---|---|
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1138268 A1 | 10/2001 |
| EP | 1302169 A1 | 4/2003 |
| EP | 1330987 A1 | 7/2003 |
| EP | 1854433 A1 | 11/2007 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 99/59669 | 11/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084768 A2 | 10/2004 |
| WO | WO 2005/002474 A1 | 1/2005 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

"Tecnica Operatoria Per Il Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.
Benzel et al., "Posterior Cervical Interspinous Compression Wiring and Fusion for Mid to Low Cervical Spinal Injuries," J. Neurosurg., Jun. 1989, pp. 893-899, vol. 70.
Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.
Christie et al., "Dynamic Interspinous Process Technology," SPINE, 2005, pp. S73-S78, vol. 30, No. 16S.
Cousin Biotech, "Analysis of Clinical Experience with a Posterior Shock-Absorbing Implant," date unknown, pp. 2-9.
Cousin Biotech, Dispositif Intervertébral Amortissant, Jun. 1998, pp. 1-4.
Cousin Biotech, Technique Operatoire de la Prothese DIAM, date unknown, Annexe 1, pp. 1-8.
Dickman et al., "The Interspinous Method of Posterior Atlantoaxial Arthrodesis," J. Neurosurg., Feb. 1991, pp. 190-198, vol. 74.
Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Duff, "Methyl Methacrylate in Spinal Stabilization," Techniques in Spinal Fusion and Stabilization, Hitchon et al., eds., 1995, pp. 147-151, Ch. 14, Thieme, New York.
Ebara et al., "Inoperative Measurement of Lumbar Spinal Instability," SPINE, 1992, pp. S44-S50, vol. 17, No. 3S.
Fassio et al., "Treatment of Degenerative Lumbar Spinal Instability L4-L5 by Interspinous Ligamentoplasty," Rachis, Dec. 1991, pp. 465-474, vol. 3, No. 6.
Fassio, "Mise au Point Sur la Ligamentoplastie Inter-Epineuse Lombaire Dans les Instabilites," Maîtrise Orthopédique, Jul. 1993, pp. 18, No. 25.
Garner et al., "Development and Preclinical Testing of a New Tension-Band Device for the Spine: the Loop System," Eur. Spine J., Aug. 7, 2002, pp. S186-S191, vol. 11, Suppl. 2.
Guang et al., "Interspinous Process Segmental Instrumentation with Bone-Button-Wire for Correction of Scoliosis," Chinese Medical J., 1990, pp. 721-725, vol. 103.
Guizzardi et al., "The Use of Diam (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring-Bone Grafting for Spondylolysis and Spondylolisthesis," SPINE, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Kramer et al., "Intervetertebral Disk Diseases: Causes, Diagnosis, Treatment and Prophylaxis," pp. 244-249, Medical, 1990.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.
Müller, "Restauration Dynamique de la Stabilité Rachidienne," Tiré de la Sulzer Technical Review, Jan. 1999, Sulzer Management Ltd, Winterthur, Switzerland.
Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.
Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.
Petrini et al., "Stabilizzazione Elastica," Patologia Degenerativa del Rachide Lombare, Oct. 5-6, 2001, Rimini.
Porter, "Spinal Stenosis and Neurogenic Claudication," SPINE, Sep. 1, 1996, pp. 2046-2052, vol. 21, No. 17.

(56) References Cited

OTHER PUBLICATIONS

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrate Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. 5164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zdeblick et al., "Two-Point Fixation of the Lumbar Spine Differential Stability in Rotation," SPINE, 1991, pp. S298-S301, vol. 16, No. 6, Supplement.

Zucherman et al., "Clinical Efficacy of Spinal Instrumentation in Lumbar Degenerative Disc Desease," SPINE, Jul. 1992, pp. 834-837, vol. 17, No. 7.

* cited by examiner

INJECTABLE FLEXIBLE INTERSPINOUS PROCESS DEVICE SYSTEM

BACKGROUND

This invention relates generally to the treatment of spinal conditions, and more particularly, to the treatment of spinal stenosis using devices for implantation between adjacent spinous processes.

The spine is divided into regions that include the cervical, thoracic, lumbar, and sacrococcygeal regions. The cervical region includes the top seven vertebrae identified as C1-C7. The thoracic region includes the next twelve vertebrae identified as T1-T12. The lumbar region includes five vertebrae L1-L5. The sacrococcygeal region includes nine fused vertebrae that make up the sacrum and the coccyx. The vertebrae of the sacrum are identified as the S1-S5 vertebrae. Four or five rudimentary members form the coccyx.

The clinical syndrome of neurogenic intermittent claudication due to lumbar spinal stenosis is a frequent source of pain in the lower back and extremities, leading to impaired walking, and causing other forms of disability in the elderly. Although the incidence and prevalence of symptomatic lumbar spinal stenosis have not been established, this condition is the most frequent indication of spinal surgery in patients older than 65 years of age.

Lumbar spinal stenosis is a condition of the spine characterized by a narrowing of the lumbar spinal canal. With spinal stenosis, the spinal canal narrows and pinches the spinal cord and nerves, causing pain in the back and legs. It is estimated that approximately 5 in 10,000 people develop lumbar spinal stenosis each year. For patients who seek the aid of a physician for back pain, approximately 12%-15% are diagnosed as having lumbar spinal stenosis.

Common treatments for lumbar spinal stenosis include physical therapy (including changes in posture), medication, and occasionally surgery. Changes in posture and physical therapy may be effective in flexing the spine to decompress and enlarge the space available to the spinal cord and nerves—thus relieving pressure on pinched nerves. Medications such as NSAIDS and other anti-inflammatory medications are often used to alleviate pain, although they are not typically effective at addressing spinal compression, which is the cause of the pain.

Surgical treatments are more aggressive than medication or physical therapy, and in appropriate cases surgery may be the best way to achieve lessening of the symptoms of lumbar spinal stenosis. The principal goal of surgery is to decompress the central spinal canal and the neural foramina, creating more space and eliminating pressure on the spinal nerve roots. The most common surgery for treatment of lumbar spinal stenosis is direct decompression via a laminectomy and partial facetectomy. In this procedure, the patient is given a general anesthesia and an incision is made in the patient to access the spine. The lamina of one or more vertebrae is removed to create more space for the nerves. The intervertebral disc may also be removed, and the adjacent vertebrae may be fused to strengthen the unstable segments. The success rate of decompressive laminectomy has been reported to be in excess of 65%. A significant reduction of the symptoms of lumbar spinal stenosis is also achieved in many of these cases.

Alternatively, the vertebrae can be distracted and an interspinous process device implanted between adjacent spinous processes of the vertebrae to maintain the desired separation between the vertebral segments. Such interspinous process devices typically work for their intended purposes but they could be improved. Current devices for spacing adjacent interspinous processes are typically preformed, and are not customizable for different sizes and dimensions of the anatomy of an interspinous space of an actual patient. Instead, preformed devices of an approximately correct size are inserted into the interspinous space of the patient. Unfortunately, because of individual differences in patient anatomy, it is possible that such preformed devices may not comfortably fit in the interspinous space. Moreover, current devices may be difficult to implant because of the tissue obstructing the interspinous space. The necessity to have a configuration for current devices that ensures that the device remains in the proper location may also make it difficult to implant the device in a minimally invasive or percutaneous manner. Further, current devices are relatively stiff, which may cause subsidence in the spinous processes contacting the device after implantation. Thus a need exists for improvements to surgical spacers, such as those for spacing adjacent interspinous processes.

SUMMARY

An injectable, flexible interspinous process device is described herein. The interspinous process device is flexible and can be fillable in situ with a desired amount of material such as a biocompatible fluid. In addition, the interspinous process device is substantially impervious to the material with which it will be filled, although the interspinous process device may be permeable to other materials if desired. The interspinous process device is formed from an outer container portion and contains a supporting element such as a mesh or tube that provides added structural support to the container. The supporting element may be self-expanding to facilitate expansion of the device in situ. The supporting element may be located adjacent to an inner surface of the container, although it may be located within the container material itself or bonded to the outer surface of the container material.

As mentioned above, the supporting element may be self expanding so that once the interspinous process device is delivered to the desired position and any constraints removed, the interspinous process device will be deployed to its desired final configuration. The interspinous process device may then be filled with a suitable material such as a biocompatible fluid or a material that is in a liquid state when the interspinous process device is being filled but cures to a more viscous, or generally solid state after the interspinous process device is filled. The interspinous process device has a deployed configuration that includes a central spacer portion that is adapted to be disposed in the interspinous space and enlarged proximal and distal portions that prevent the interspinous process device from moving proximally or distally out of the interspinous process space.

A conduit is coupled to the interspinous process device and is long enough so that it can extend from the interspinous process device to a position outside of the patient to allow for easy manipulation by the surgeon. The conduit thus allows the interspinous process device to be filled with the desired filler material. A breakaway seal may be formed at the interface of the conduit and the interspinous process device. Alternatively, a valve may be located at that location. With either embodiment, the surgeon can inject a material into the interspinous process device to provide the device with its desired final flexibility characteristic and then remove the conduit from the interspinous process device without the injected material flowing back out of the interspinous process device.

A delivery system is also provided for delivering the flexible interspinous process device described above to a desired location. The interspinous process device is in an undeployed, low profile state when it is delivered to the desired location. The delivery system includes an outer catheter that is disposed over the interspinous process device to maintain it in the undeployed state and thus facilitate delivery of the device to the desired location in a minimally invasive or percutaneous manner. If desired, a guidewire may be used to provide a track along which the delivery device can be advanced to simplify the delivery of the interspinous process device to the desired location. Alternatively, the delivery device may include a steerable catheter to facilitate delivery of the interspinous process device to the desired location. The delivery system may also include an outer cannula disposed about the outer catheter. The outer cannula provides added protection to the container to prevent damage to the container during delivery of the interspinous process device through the patient's anatomy to the desired location in the spine. The outer cannula may be relatively stiff. This allows the surgeon to push against the delivery system and facilitates the movement of the delivery system through the patient's anatomy.

In addition, an inner retractable sleeve may be located inside the interspinous process device to hold the supporting element in an undeployed configuration and allows the surgeon to control the deployment of the supporting element once the interspinous process device is located in the desired position. Of course, where the supporting element is located within the material of the container, or bonded to the container, the inner sleeve may not be needed. However, in such an arrangement, the container material for the interspinous process device should be strong enough to resist tearing when the supporting element becomes unconstrained and is allowed to deploy. Where an inner sleeve and/or guidewire is used with the delivery system, the proximal end of the interspinous process device has a self sealing feature that allows the inner sleeve and/or guidewire to be removed without compromising the fluid-tight integrity of the device.

DETAILED DESCRIPTION

As used in this specification and the appended claims, the singular forms "a," "an" and "the" include plural referents unless the context clearly dictates otherwise. Thus, for example, the term "a member" is intended to mean a single member or a combination of members, and "a material" is intended to mean one or more materials, or a combination thereof. Furthermore, the words "proximal" and "distal" refer to directions closer to and away from, respectively, an operator (e.g., surgeon, physician, nurse, technician, etc.) who would insert the medical device into the patient, with the tip-end (i.e., distal end) of the device inserted inside a patient's body first. Thus, for example, the device end first inserted inside the patient's body would be the distal end of the device, while the device end last to enter the patient's body would be the proximal end of the device.

As used in this specification and the appended claims, the term "body" when used in connection with the location where the device of this invention is to be placed to treat lumbar spinal stenosis, or to teach or practice implantation methods for the device, means a mammalian body or a model of a mammalian body. For example, a body can be a patient's body, or a cadaver, or a portion of a patient's body or a portion of a cadaver or a model of any of the foregoing.

As used in this specification and the appended claims, the term "parallel" describes a relationship, given normal manufacturing or measurement or similar tolerances, between two geometric constructions (e.g., two lines, two planes, a line and a plane, two curved surfaces, a line and a curved surface or the like) in which the two geometric constructions are substantially non-intersecting as they extend substantially to infinity. For example, as used herein, a line is said to be parallel to a curved surface when the line and the curved surface do not intersect as they extend to infinity. Similarly, when a planar surface (i.e., a two-dimensional surface) is said to be parallel to a line, every point along the line is spaded apart from the nearest portion of the surface by a substantially equal distance. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

As used in this specification and the appended claims, the terms "normal", "perpendicular" and "orthogonal" describe a relationship between two geometric constructions (e.g., two lines, two planes, a line and a plane, two curved surfaces, a line and a curved surface or the like) in which the two geometric constructions intersect at an angle of approximately 90 degrees within at least one plane. For example, as used herein, a line is said to be normal, perpendicular or orthogonal to a curved surface when the line and the curved surface intersect at an angle of approximately 90 degrees within a plane. Two geometric constructions are described herein as being "normal", "perpendicular", "orthogonal" or "substantially normal", "substantially perpendicular", "substantially orthogonal" to each other when they are nominally 90 degrees to each other, such as for example, when they are 90 degrees to each other within a tolerance. Such tolerances can include, for example, manufacturing tolerances, measurement tolerances or the like.

An injectable, flexible interspinous process device is described herein. The interspinous process device 100 includes a container 110, which is flexible and can be fillable in situ with a desired amount of material, such as a biocompatible fluid. Container 110 may be formed from a flexible material that may be compliant or non-compliant. The material may also be tear resistant. The material may also be substantially fluid impermeable so that the material that is used to fill container 110 will not leak from container 110. For example, container 110 may be formed from a silicone material provided by NuSil Technology LLC. Other silicone and polymeric materials may also be used to form container 110. In addition to being flexible, tear resistant and fluid impermeable, the material used to form container 110 may be self-sealing to allow elements of a delivery system or other elements of interspinous process device 100 to be inserted in and removed from container 110 without permanently compromising the fluid impermeable nature of the material that forms container 110.

Figure 1A:
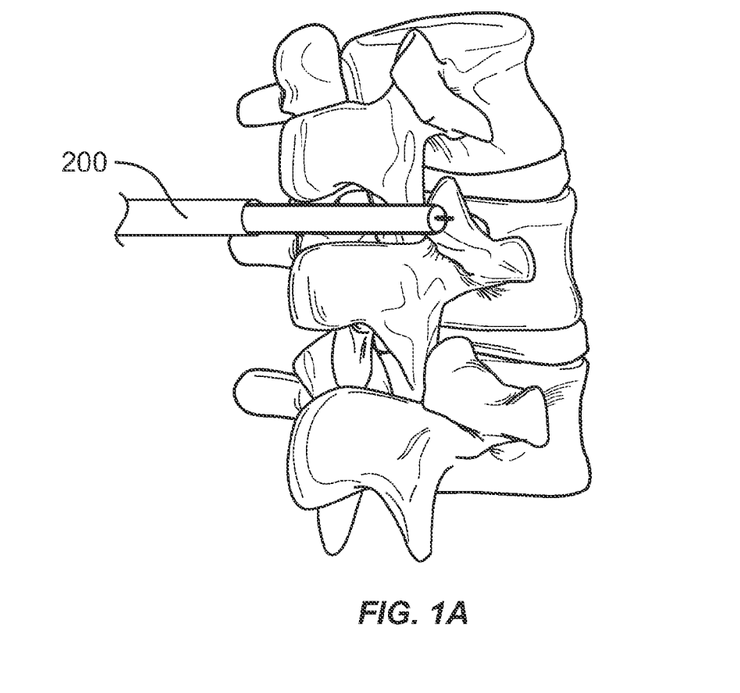
FIG. 1A is a rear perspective view of an undeployed flexible interspinous process device and delivery system and a portion of a spine on which the flexible interspinous process device is to be located.
Figure 1B:
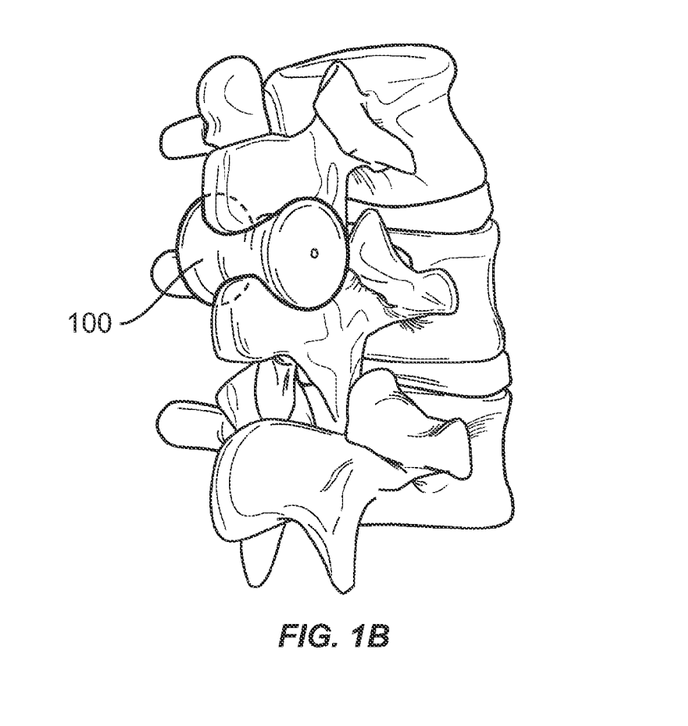
FIG. 1B is a rear perspective view of a deployed flexible interspinous process device and a portion of a spine on which it is located.
Figures 2A, 2B:
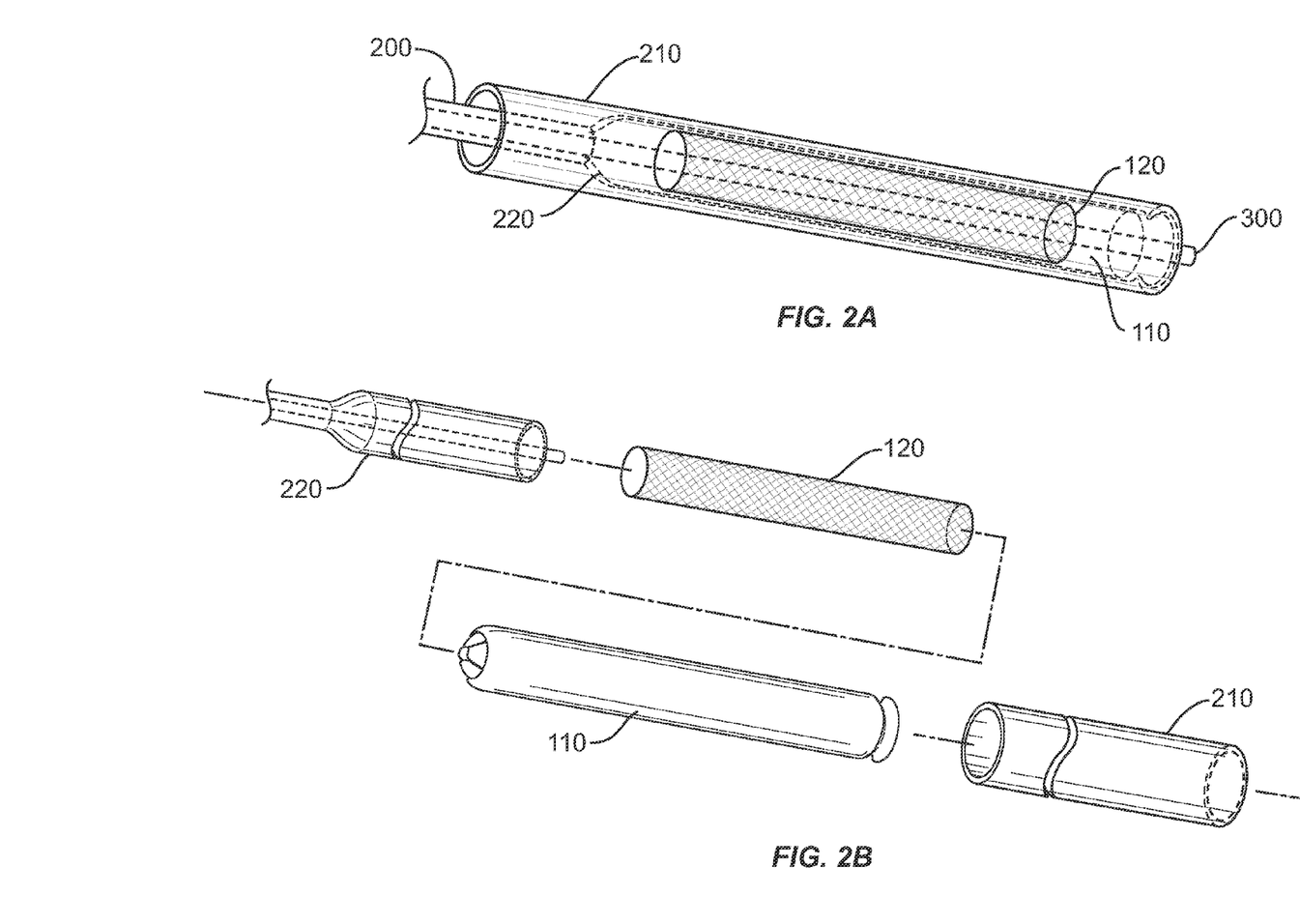
FIG. 2A is a perspective view of the flexible interspinous device and delivery system shown in FIG. 1A, partially expanded for clarity.
FIG. 2B is an exploded, perspective view of the flexible interspinous process device and delivery system shown in FIG. 2A.
Figure 3A:
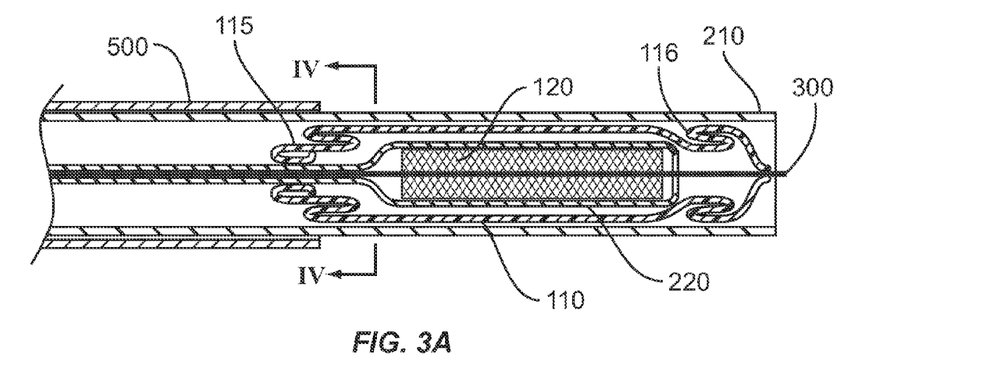
FIG. 3A is a cross-sectional view of an interspinous process device and delivery system, partially expanded for clarity.
Figure 3B:
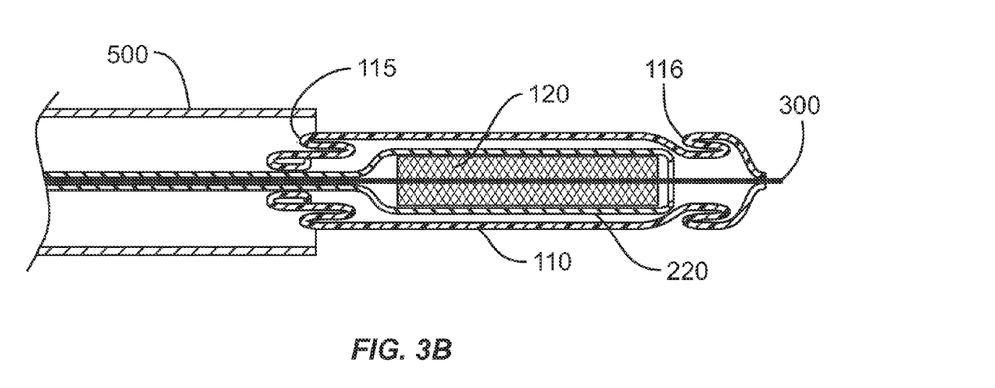
FIG. 3B is a cross-sectional view of the interspinous process device and the delivery system shown in FIG. 3A with the outer catheter removed from around the interspinous process device.
Figure 3C:
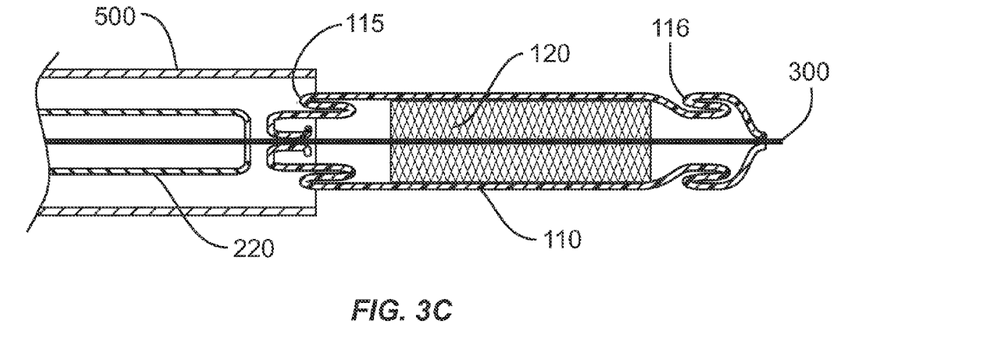
FIG. 3C is a cross-sectional view of the interspinous process device and the delivery system shown in FIG. 3A with the outer and inner catheters removed from the interspinous process device.
Figure 3D:
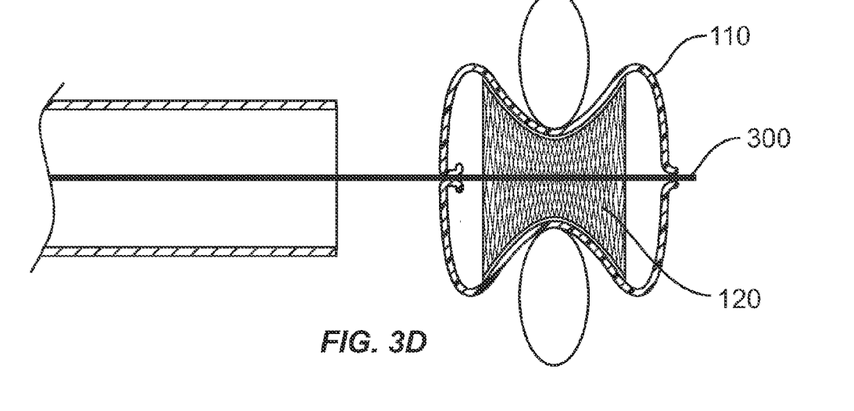
FIG. 3D is a cross-sectional view of a fully deployed interspinous process device that is located between two spinous processes.
Figure 3E:
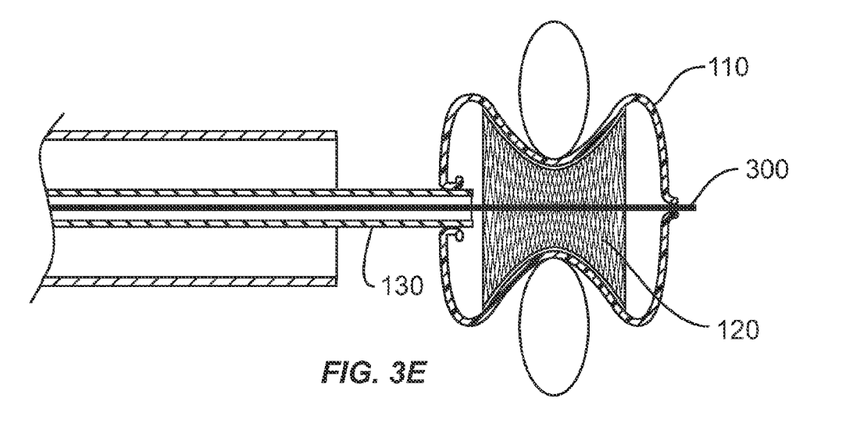
FIG. 3E is a cross-sectional view of a fully deployed interspinous process device that is located between two spinous processes and that has a fill tube removably attached to the interspinous process device.
Figure 3F:
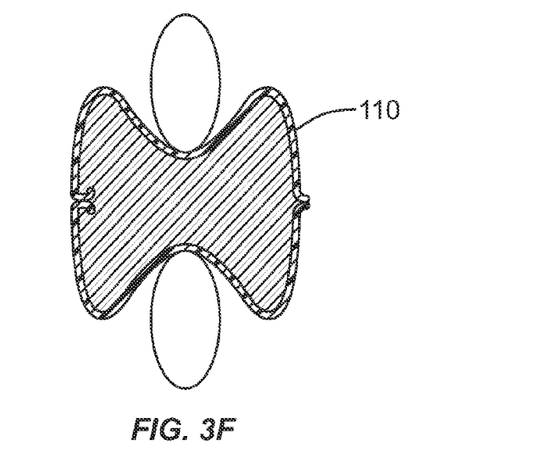
FIG. 3F is a cross-sectional view of a fully deployed interspinous process device that has been filled with a fluid.

Container 110 is formed from a flexible material so that it can be folded in a first configuration having a low profile and unfolded into a second configuration having a larger profile. In its low profile configuration, container 110 should have a cross-section that allows it to be inserted into the interspinous space with minimal disruption to the surrounding tissue. Thus, container 110 may be delivered in a minimally invasive or percutaneous manner to the desired location in the anatomy. Container 110 has a proximal portion, a distal portion and a medial portion. In the first, low profile configuration, container 110 is folded such that the proximal portion, the medial portion and the distal portion have substantially the same height. In the second, larger profile configuration, see e.g. FIG. 3F, the proximal portion and distal portion each has a height that is larger than the height of the medial portion. This allows the proximal portion and the distal portion of container 110 to extend along at least a portion of the height of each of the two adjacent spinous processes between which container 110 is implanted. The medial portion has a height that maintains the desired space between the two adjacent spinous process between which container 110 is implanted.

Interspinous process device 100 also includes a support member 120 that may be formed as a mesh or tube and that may be self-expanding. Support member 120 may be formed from a metallic material and may be a shape memory material. Support member 120 may extend along the medial portion. Support member 120 has a generally tubular deployed configuration that generally matches the configuration of the medial portion when container 110 is deployed. If desired, support member 120 may also extend along the proximal and distal portions. In this case, support member 120 would have an enlarged proximal portion and an enlarged distal portion that would generally match the overall configuration of container 110, including its proximal and distal portions, when container 110 is deployed. The use of a metallic support member also helps the surgeon visualize the location of interspinous process device under fluoroscopy.

Support member 120 is located inside and adjacent to the inner surface of container 110, although it may be located within the container material itself such that support member 120 may be located within the sidewall container 110. In addition, support member may be bonded to the outside surface of container 110. With self expanding support member 120 contacting container 110, support member 120 moves the medial portion to its unfolded, larger profile configuration, as well as the proximal and distal portions if support member 120 extends along the proximal and distal portions. Container 110 may then be filled with a suitable material such as a biocompatible fluid or a material that is initially a liquid and then cures to a more viscous state or to a solid state. Thus, container 110 may be easily filled and then when the filler material cures, container 110, along with support member 120, will provide adequate support between the two adjacent spinous processes to maintain the desired distraction therebetween. In addition, when the proximal portion and the distal portion are in their unfolded configurations and filled with the filler material, the proximal portion and distal portion prevent the interspinous process device 100 from moving proximally or distally out of the interspinous process space. The volume of material injected into container 110 may be varied to vary the stiffness/flexibility of medial portion 113 as determined by the surgeon.

A conduit 130 is coupled to container 110 and is long enough so that it can extend from container 110 to a position outside of the patient to allow for easy manipulation by the surgeon. Conduit 130 allows container 110 to be filled with the desired flowable material. A breakaway seal may be formed at the interface of conduit 130 and container 110 or a valve 400 may be located at that position. Alternatively, the fillable material may seal the interface between container 110 and conduit 130 when the fillable material cures. In such an embodiment, conduit 130 is connected to container 110 with a frangible connection and no seal. With any of the foregoing embodiments, the surgeon can inject a flowable material into interspinous process device 100 to provide the device with its desired final flexibility characteristic and remove conduit 130 from interspinous process device 100 without the injected material flowing back out of interspinous process device 100.

A delivery device 200 is also provided for implanting interspinous process device 100 described above. Delivery device 200 includes an outer catheter 210. Delivery device 200 may also include a cannula 500 disposed about outer catheter 210. Cannula 500 protects container 110 during delivery of interspinous process device 100 to the desired location in the patient's anatomy. It is also relatively stiff and thus is more easily manipulated by the surgeon during implantation of interspinous process device 100. It is to be noted that although the FIGS. show delivery device 200 being inserted from the left side of a prone patient, delivery device 200 may also be inserted into the right side of a prone patient. It is also within the scope of this invention that delivery device could be inserted in an anterior, lateral to medial approach.

Figure 4:
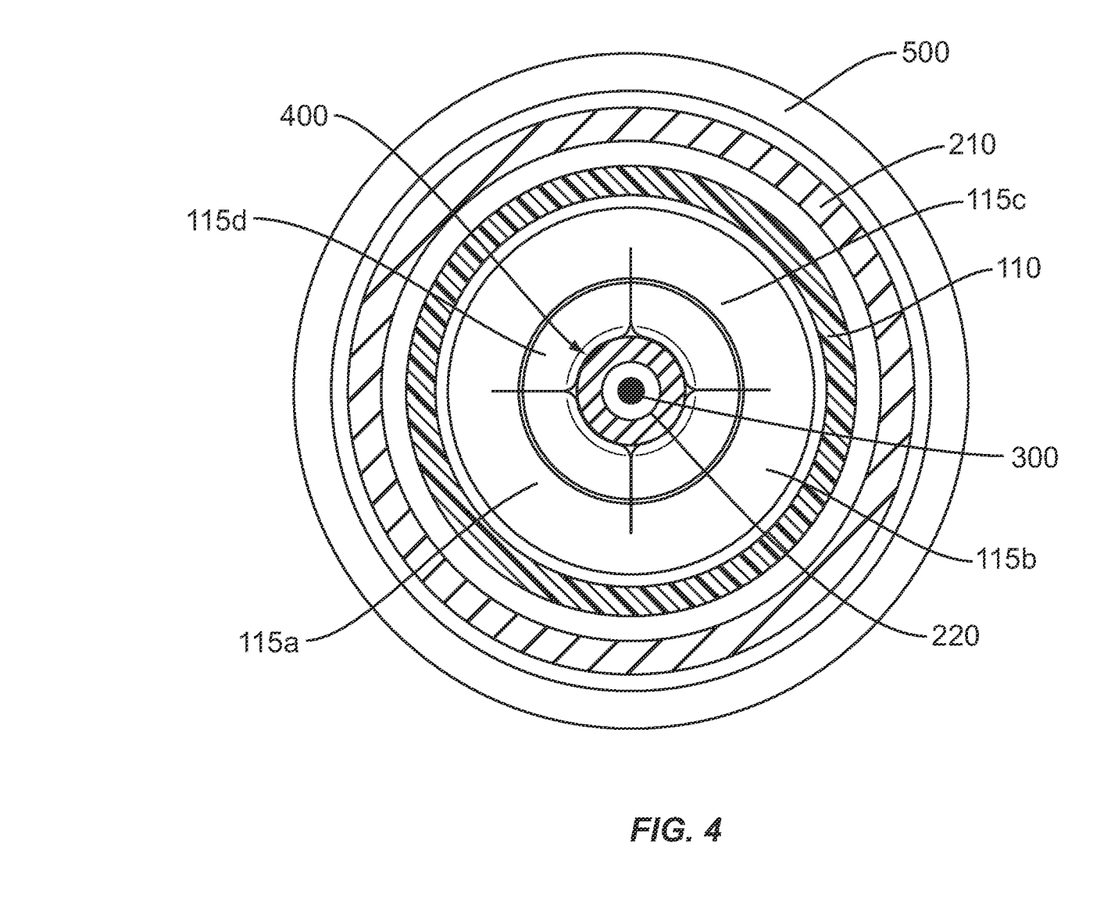
FIG. 4 is a cross-sectional view of the interspinous process device and delivery system shown in FIG. 3A taken along line IV-IV.

Delivery device 200 may also include an inner catheter 220. In addition, if desired, a guidewire 300 may also be used in conjunction with delivery device 200. Outer catheter 210 is disposed over interspinous process device 100 to maintain it in the collapsed state against the force exerted against container 110 by support member 120. This allows interspinous process device 100 to be delivered to the desired location in a minimally invasive or percutaneous manner. In addition, an inner retractable sleeve 220 may be located inside interspinous process device 100 to hold support member 120 in an undeployed configuration. Inner retractable sleeve 220 allows for more controlled deployment of support member 120 when outer catheter 210 is removed from around undeployed interspinous process device 100 since the surgeon may slowly remove inner retractable sleeve 220 from around support member 120 and confirm, under fluoroscopy, its proper location during this removal step. Of course, where support member 120 is located within the wall of container 110 or bonded to either the inner wall or outer wall of container 110, it may not be necessary to use inner retractable sleeve 220. With this configuration, the surgeon would simply use outer catheter 210 to control deployment of support member 120. The surgeon would slowly remove outer catheter 210 from around container 110 to control its deployment and confirm that it is properly positioned before completely removing outer catheter 210 from around support member 120 and container 110.

Where inner retractable sleeve 220 is used with delivery device 200, the proximal end of container 110 has a self sealing feature that allows inner retractable sleeve 220 to be removed without compromising the fluid-tight integrity of container 110. For example, the proximal portion may have a proximal face that is formed from a plurality of flaps. As shown, for example, in FIG. 4, four such flaps 115a, 115b, 115c and 115d are formed in the proximal face. Flaps 115a, 115b, 115c and 115d are connected to the remainder of container 110 in a resilient manner so that they are biased in a closed position but are able to bend or flex in a generally proximal direction. This allows inner retractable sleeve 220 to be removed from the inside of container 110 through the proximal end thereof. In addition, the inner portion of support member 120 may be coated with silicone or other biocompatible, lubricious material to provide a lubricious surface and facilitate the removal of inner retractable sleeve 220 from container 110. Once inner retractable sleeve 220 has been removed, the natural bias of flaps 115a, 115b, 115c and 115d closes the proximal end of container 110. Where the filler material for interspinous process device 100 is curable, flaps 115a, 115b, 115c and 115d will be sealed by the filler material to maintain the integrity of interspinous process device 100. As such, inner retractable sleeve 220 is typically removed from interspinous process device 100 after it has been located in the desired position within the interspinous space of interest and after the filler material has been injected into container 110 but before the filler material has cured.

Guidewire 300 may be used to provide a track along which delivery device 200 can be advanced to simplify the delivery of interspinous process device 100 to the desired location. For example, guidewire 300 may be inserted into a patient and maneuvered by the surgeon through the interspinous ligament to the interspinous process space of interest and as far anterior in that space as possible. It may be necessary to disrupt and dislodge any soft tissue in the interspinous space to ensure proper placement of interspinous process device 100. An appropriate curette or other cutting device (not shown) may be disposed over guidewire 300 and maneuvered over guidewire 300, which acts as a track for the cutting device, to the desired location to remove the unwanted tissue. Alternatively, the cutting device does not have to be delivered to the interspinous space over guidewire 300. Delivery device 200, with interspinous process device 100 therein, is then maneuvered over guidewire 300 until interspinous process device 100 is in the desired location. Guidewire 300 can be removed at this point. Alternatively, a guidewire does not have to be used and instead outer catheter 210 may be steerable. If desired, both guidewire 300 and a steerable outer catheter 210 may be used together.

Once interspinous process device 100 is in the desired position, delivery device 200 can be withdrawn from the patient. With the removal of delivery device 200, outer catheter 210 no longer constrains support member 120. Where inner retractable sleeve 220 is not in use, this allows support member 120 to be deployed and move container 110 to its unfolded larger profile configuration. Where inner retractable sleeve 220 is used to control deployment of support member 120, inner retractable sleeve 220 is removed from container 110 through flaps 115a, 115b, 115c and 115d. Thereafter, the filler material may be injected into container 110 until interspinous process device 100 has reached its desired stiffness/flexibility. The filler material may include barium sulfate to aid in visualization of interspinous process device 100 under fluoroscopy so the surgeon can confirm that interspinous process device 100 is in the proper location and is properly deployed. Barium sulfate may not be needed where support member 120 is formed from a material that is visible under fluoroscopy. Once the surgeon is satisfied that interspinous process device 100 has been appropriately deployed, conduit 130 may be removed.

While various embodiments of the flexible interspinous process device and delivery system have been described above, it should be understood that they have been presented by way of example only, and not limitation. Many modifications and variations will be apparent to the practitioner skilled in the art. The foregoing description of the flexible interspinous process device and delivery device is not intended to be exhaustive or to limit the scope of the invention. It is intended that the scope of the invention be defined by the following claims and their equivalents.

What is claimed is:

1. An implantable device and delivery system, comprising:
a flexible container configured to be filled with material in situ having a proximal portion, a medial portion and a distal portion, the flexible container being movable from an undeployed configuration to a deployed configuration and wherein the proximal portion defines a first proximal height in the undeployed configuration and a second proximal height in the deployed configuration, the medial portion defines a first medial height in the undeployed configuration and a second medial height in the deployed configuration and the distal portion defines a first distal height in the undeployed configuration a second distal height in the deployed configuration and wherein the first proximal height, the first medial height and the first distal height are substantially the same and the second proximal height and the second distal height are larger than the second medial height;
a support element disposed within the flexible container along the medial portion, the support member configured to expand the medial portion from the undeployed configuration to the deployed configuration;
an inner removable sleeve disposed within the flexible container adjacent to the support element; and
an outer catheter removably disposed about the flexible container to maintain the flexible container in the undeployed configuration.

2. The implantable device and delivery system of claim 1 wherein the support element is coated with silicone.

3. The implantable device and delivery system of claim 1 wherein the support element is a mesh.

4. The implantable device and delivery system of claim 3 wherein the mesh is self-expanding.

5. The implantable device and delivery system of claim 1 wherein the proximal portion includes a plurality of resealable flaps that define a closable opening along a proximal face of the container and which are adapted to allow the removable inner sleeve to be removed from the container.

6. The implantable device and delivery system of claim 5 wherein the plurality of flaps are biased to a closed position.

7. The implantable device and delivery system of claim 5 wherein the flexible container is formed from a self-sealing material.

8. The implantable device and delivery system of claim 1 wherein the outer catheter is steerable.

9. The implantable device and delivery system of claim 1 further comprising a cannula disposed about the outer catheter.

10. The implantable device and delivery system of claim 1 wherein the proximal portion and the distal portion are folded in the undeployed configuration.

11. A method comprising; providing the device of claim 1; disposing the device within an outer catheter to maintain the device in the undeployed configuration; delivering the device and a distal portion of the outer catheter to a desired location within a patient's anatomy; removing the outer catheter from the desired location; filling the device with a biocompatible material in situ when the device is in the deployed configuration.

12. The method of claim 11 further including providing a removable inner sleeve within the container adjacent to the support element.

13. The method of claim 12 wherein filling the device occurs when the biocompatible material is a fluid and further comprising allowing the biocompatible material to reach a final cure state and removing the removable inner sleeve from the container prior to the final cure state.

14. The method of claim 11 further comprising allowing the support element to expand the flexible container in situ.

15. The method of claim 14 wherein filling the device with a biocompatible material is performed after allowing the support element to expand the flexible container in situ.

16. The method of claim 11 further comprising inserting a guidewire into the patient and disposing the guidewire such that a distal portion of the guidewire is located between two adjacent spinous processes of the patient.

17. The method of claim 16 advancing the device and outer catheter over the guidewire.

18. The method of claim 16 wherein the desired location is an interspinous space defined by a superior spinous process and an inferior spinous process.

19. The method of claim 18 further comprising dislodging any soft tissue located in the interspinous space.

20. The method of claim 19 wherein the disruption is performed with a curette.

* * * * *